(12) United States Patent
Wallace et al.

(10) Patent No.: US 7,326,809 B2
(45) Date of Patent: Feb. 5, 2008

(54) SALTS OF 4- OR 5-AMINOSALICYLIC ACID

(75) Inventors: John L. Wallace, Cochrane (CA); Giuseppe Cirino, Naples (CA); Anna Sparatore, Milan (IT)

(73) Assignee: Antibe Therapeutics Inc., Calgary (CA)

( * ) Notice: Subject to any disclaimer, the term of this patent is extended or adjusted under 35 U.S.C. 154(b) by 152 days.

(21) Appl. No.: 10/908,856

(22) Filed: May 27, 2005

(65) Prior Publication Data

US 2006/0003972 A1    Jan. 5, 2006

(30) Foreign Application Priority Data

May 27, 2004   (EP) .................................. 04425384

(51) Int. Cl.
*C07C 229/00* (2006.01)

(52) U.S. Cl. ...................... 562/453; 514/163; 514/419; 514/561

(58) Field of Classification Search ................. 562/453
See application file for complete search history.

(56) References Cited

U.S. PATENT DOCUMENTS 4,632,921 A * 12/1986 Bauer .......................... 514/163
6,271,278 B1 * 8/2001 Park et al. ................... 521/150
6,323,234 B1    11/2001 Garvey et al.

OTHER PUBLICATIONS

Akisu, M. et al, "Protective Effect of Dietary Supplements with L-Arginine and L-Carnitine on Hypoxia/Reoxygenation—Induced Necrotizing Entrocolitis in Young Mice", Biol. Neonate (2002), 81, 260-5.
Di Lorenzo, M et al, "Use of L-Arginine in the Treatment of Experimental Necrotizing Entercolitis", J. Pediatr. Surg, (1995), 30, 235-240.
Kubes, P, "Ischemia-Reperfusion in Feline Small Intestine: A Role for Nitric Oxide", AM. J. Physiol, (1993), 264, G143-9.
Goebell, H, et al, "Oroileal Transit of Slow Release 5-Aminosalicylic Acid" Gut, (1993), 34, 669-75.
Wallace, J. L. et al, "Enhanced Anti-Inflammatory Effects of a Nitric Oxide-Releasing Derivative of Mesalamine in Rats", Gastroenterology (1999), 117, 557-66.

* cited by examiner

*Primary Examiner*—Yvonne Eyler
*Assistant Examiner*—Sudhakar Katakam
(74) *Attorney, Agent, or Firm*—Bennett Jones LLP

(57) ABSTRACT

The present invention provides L-arginine salts of 4- or 5-aminosalicylic acid, and a pharmaceutical composition containing these L-arginine salts of 4- or 5-aminosalicylic acid as active ingredients, useful for the treatment of an inflammatory condition of the GI tract such as inflammatory bowel disease (IBD) and irritable bowel syndrome (IBS).

7 Claims, 11 Drawing Sheets

*p<0.05

**p<0.01

*p<0.05

*p<0.05

**p<0.01

**p<0.01

*p<0.05, **p<0.01

*p<0.05

*p<0.05

SALTS OF 4- OR 5-AMINOSALICYLIC ACID

This application claims the benefit of European Patent Office Doc. No. 04425384.7, filed May 27, 2004.

FIELD OF THE INVENTION

The present invention relates to a salt of 4- or 5-aminosalicylic acid (4- or 5-ASA) useful in the treatment of intestinal diseases such as inflammatory bowel disease (IBD) and irritable bowel syndrome (IBS). In particular, the present invention relates to an L-arginine salt of 4- or 5-ASA and pharmaceutical compositions thereof.

BACKGROUND OF THE INVENTION

Inflammatory bowel disease (IBD) is the general name for diseases that cause inflammation in the small intestine and colon. Ulcerative colitis is the most common inflammatory bowel disease and it affects various portions of the gastrointestinal (GI) tract, particularly the lower GI tract, and more particularly the colon and/or rectum. A second IBD is Crohn's disease, which predominates in the small intestine (ileum) and the large intestine (colon).

Ulcerative colitis can be difficult to diagnose in that its symptoms are similar to other intestinal disorders and to Crohn's disease. Crohn's disease differs from ulcerative colitis because it causes deeper inflammation into the intestinal wall. Also, Crohn's disease usually occurs in the small intestine, although it can also occur in the mouth, esophagus, stomach, duodenum, large intestine, appendix, and anus.

Ulcerative colitis may occur in people of any age, but most often it starts between ages 15 and 30, or less frequently between ages 50 and 70. Children and adolescents sometimes develop this disease. Ulcerative colitis affects men and women equally and appears to run in some families.

It is also important to consider that about 5 percent of people with ulcerative colitis develop colon cancer. The risk of cancer increases with the duration and the extent of involvement of the colon. For example, if only the lower colon and rectum are involved, the risk of cancer is no higher than normal. However, if the entire colon is involved, the risk of cancer may be as much as 32 times the normal rate. Thus, it is possible that drugs useful in the treatment of IBD may also be useful in the prevention of colon cancer.

The pathogenesis of IBD likely involves multifactorial interactions among genetic factors, immunological factors and environmental triggers. Recent evidence suggests that a pathologic activation of the mucosal immune system in response to antigens is a key factor in the pathogenesis of IBD.

The presentation of antigen in the inflammatory process is closely followed by generation of cytokines, small glycoprotein peptide molecules, which provide signals for the communication among different cell populations determining the direction of subsequent immune and inflammatory response. Pro-inflammatory cytokines include interleukin (IL)-1, IL-6, IL-8 and tumor necrosis factor-alpha (TNF-α). Macrophages are the major source of cytokines, with epithelial cells also being able to produce a number of these peptide factors.

T helper (Th) cells are a further important source of cytokines. Th1 cells, which are associated with a cell-mediated immune response, produce IL-2, interferon gamma (IFN-γ) and TNF-α. A key transcription factor involved in the regulation of inflammation, NFkB, which is specifically implicated in the pathogenesis of IBD, regulates the amount of cytokines produced by the Th1 cells (see Neurath et al. (1996) *Nature Med.* 2: 998-1004). Th2 cells enhance antibody synthesis by B cells and produce IL-4, IL-5, IL-6, and IL-10.

Chemokines are also thought to contribute to the pathogenesis of colitis. Chemokines are pro-inflammatory proteins that participate in immune and inflammatory responses through the chemoattraction and activation of leukocytes. For example, RANTES is a C—C chemokine that promotes the recruitment and activation of inflammatory cells such as monocytes, lymphocytes, mast cells and eosinophils. RANTES has recently been shown to be elevated during the chronic phase of colitis (see Ajuebor et al. (2001) *J. Immunol.* 166: 552-558).

There is increasing evidence to show that nitric oxide, which is a free radical endogenous messenger molecule, exerts many actions in the GI tract. Recently it has been shown agents that agents that release nitric oxide (NO) in small amounts over a prolonged period of time can greatly reduce inflammation and can accelerate healing in experimental colitis. Further, an NO-releasing derivative of mesalamine has been shown to be more effective than mesalamine in reducing the severity of colitis, in particular, damage and granulocyte infiltration (see Wallace, J. L. et al. (1999) *Gastroenterology* 117: 557-66).

Nitric oxide has also been shown to be a potent mediator that induces relaxation in vascular smooth muscle and, in this manner, regulates the basal tone of the arterioles, performing an important role in the control of blood flow to the intestinal mucosa. Studies of experimental models using ischemia, hypoxia, toxins or platelet activating factor to induce intestinal damage have shown that inhibiting nitric oxide synthesis is associated with increased tissue damage whereas if it is supplied exogenously the effect is attenuated (Payne, D. and Kubes, P. (1993) *Am. J Physiol.* 265: G189-95; Caplan, M. S. et al. (1993) *Gastroenterol.* 28: 149-54; Kubes, P. (1993) *Am. J Physiol.* 264: G143-9).

Arginine is an amino acid that is a source of nitrogen for nitric oxide production. It has previously been shown that a continuous infusion of arginine attenuated intestinal injury in an experimental model and also significantly reduced intestinal tissue damage in mice subjected to hypoxia followed by re-oxygenation (Di Lorenzo, M. et al. (1995) *Pediatr. Surg.* 30: 235-40; Akisu, M. et al. (2002) *Biol. Neonate* 81:260-5).

Treatment for ulcerative colitis depends on the seriousness of the illness. Most people are treated with medication. In severe cases, a patient may need surgery to remove the diseased colon.

Irritable bowel syndrome (IBS) is a common but poorly understood disorder that causes a variety of bowel symptoms including abdominal pain, diarrhea and/or constipation, bloating, gassiness and cramping. While these symptoms may be caused by a number of different bowel diseases, IBS is usually diagnosed only after exclusion of a more serious problem. There is increasing evidence suggesting the role of inflammation in the pathogenesis of IBS.

The goal of therapy is to induce and maintain remission, and to improve the quality of life for people with IBD/IBS. Several types of drugs are available.

Aminosalicylates, which are drugs that contain 5-aminosalicylic acid (5-ASA or mesalamine) or 4-aminosalicylic acid (4-ASA), help to control the inflammation. However, both mesalamine and 4-ASA may be absorbed as it passes through the GI tract and may adversely affect the amount of mesalamine that reaches the lower GI tract, particularly the colon and rectum. Thus, various mesalamine formulations have been introduced in an attempt to protect mesalamine as it passes through the gut and upper GI tract.

In addition, several pro-drugs of mesalamine have been introduced which can aid in colon-specific delivery of mesalamine. These pro-drugs are generally less readily absorbed in the gut and upper GI tract and thus can more easily reach the colon. An example of one such drug is sulfasalazine, which is a combination of sulfapyridine and 5-ASA linked via an azo bond and is employed to induce and maintain remission. Sulfasalazine is metabolized in the body to form 5-ASA and sulfapyridine. The sulfapyridine component carries the anti-inflammatory 5-ASA to the intestine.

However, sulfapyridine may lead to side effects, such as nausea, vomiting, heartburn, diarrhea, and headache. These adverse side effects are usually attributed to the activity of sulfapyridine in the GI tract, as well as that absorbed into the system.

There is a need for a drug with improved activity over sulfazalazine without similar side effects and in the possibility of achieving such improvement with 4- or 5-ASA as the starting point.

SUMMARY OF THE INVENTION

The present invention relates to an L-arginine salt of 4- or 5-aminosalicylic acid (4- or 5-ASA) as follows:

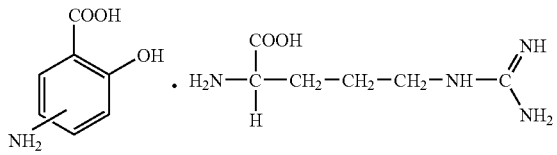

wherein —NH$_2$ is either at position 4 or 5.

In a further aspect the present invention provides a pharmaceutical composition of the L-arginine salt of 4- or 5-ASA, and a pharmaceutically acceptable excipient or carrier, particularly a pharmaceutical composition for use in the treatment of an inflammatory condition of the GI tract.

Surprisingly, the L-arginine salt of 4- or 5-ASA is more effective than 4- or 5-ASA alone in reducing inflammation. The L-arginine salts of the present invention effect a greater reduction in granulocyte infiltration (as measured by a decrease in myeloperoxidase activity) and a greater reduction in mRNA levels for IFN-γ, IL-2, TNF-α and RANTES when compared to 4- or 5-ASA alone.

More surprisingly, a greater overall reduction in colitis-associated edema, granulocyte infiltration and body weight loss is observed with the L-arginine salts of the present invention when compared to either 4- or 5-ASA alone or L-arginine alone, suggesting a synergistic effect of the combination of L-arginine and 4- or 5-ASA as a salt. Further, the L-arginine salt of 4- or 5-ASA has improved free radical scavenging properties and is a more potent anti-oxidant than 4- or 5-ASA or L-arginine. In fact, L-arginine alone showed no free radical scavenging effects and very little anti-oxidant activity. Once again, it is clearly shown that the combination of L-arginine and 4- or 5-ASA as a salt results in a synergistic enhancement of the therapeutic effect of 4- or 5-ASA.

L-arginine is a precursor in the synthesis of nitric oxide. Without being bound to any particular theory, it is thought that the L-arginine salt of the present invention may increase the levels of nitric oxide, which, in turn, will result in improved anti-inflammatory properties of the L-arginine salts of the present invention. Further, nitric oxide has been shown to have anti-oxidant activity, which may contribute to the increase in the scavenging of free radicals with the L-arginine salts of the present invention.

In one embodiment, the present invention relates to methods of treating an inflammatory condition of the GI tract, such as inflammatory bowel disease (IBD) and irritable bowel syndrome (IBS), in a subject in need of such treatment, comprising administering to the subject an effective amount of an L-arginine salt of 4- or 5-ASA.

In a further embodiment, the present invention provides the use of an L-arginine salt of 4- or 5-ASA for the manufacture of a medicament for the treatment of an inflammatory condition of the GI tract. The present invention also provides the use of an L-arginine salt of 4- or 5-ASA for the treatment of an inflammatory condition of the GI tract.

DETAILED DESCRIPTION OF THE PREFERRED EMBODIMENT

Figure 1:
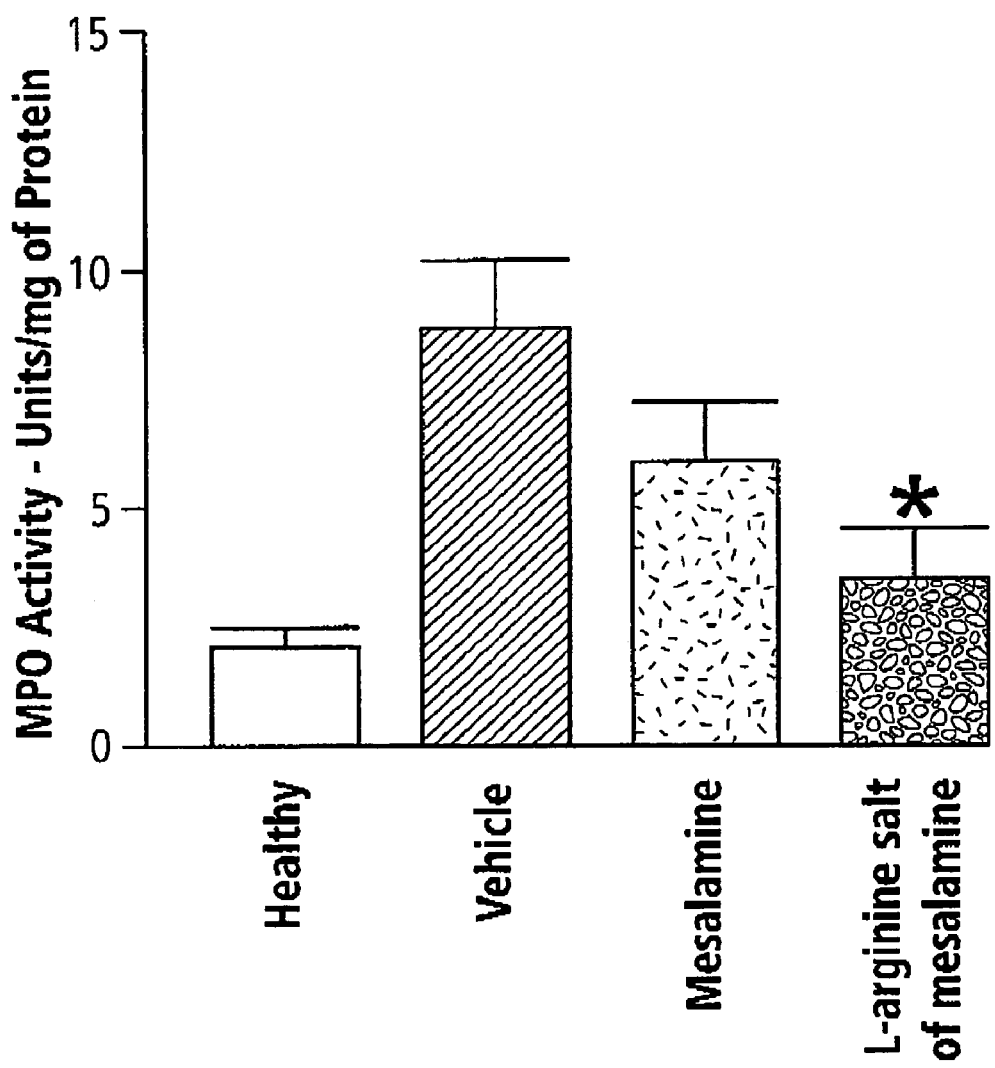
FIG. 1 shows the myeloperoxidase (MPO) activity in mice having TNBS-induced colitis after treatment with vehicle (1% CMC), 50 mg/kg mesalamine and equimolar dose of L-arginine salt of mesalamine of the present invention.

The L-arginine salt of 4- or 5-ASA of the present invention may be utilized for the prophylaxis or treatment of various diseases, particularly inflammatory conditions of the GI tract including, but not limited to, inflammatory conditions of the mouth such as mucositis, infectious diseases (e.g., viral, bacterial and fungal diseases), and Crohn's disease; inflammatory conditions of the esophagus such as esophagitis, conditions resulting from chemical injury (e.g., lye ingestion), gastroesophageal reflux disease, bile acid reflux, Barrett's esophagus, Crohn's disease, and esophageal stricture; inflammatory conditions such as gastritis (e.g., *Helicobacter pylori*, acid-peptic disease and atrophic gastritis), celiac disease, peptic ulcer disease, pre-cancerous lesions of the stomach, non-ulcer dyspepsia, and Crohn's disease; inflammatory conditions of the stomach such as Crohn's disease, bacterial overgrowth, peptic ulcer disease, and fissures of the intestine; inflammatory conditions of the colon such as Crohn's disease, ulcerative colitis, irritable bowel syndrome, infectious colitis (e.g., pseudomembranous colitis such as *Clostridium difficile* colitis, *salmonella* enteritis, *shigella* infections, yersiniosis, cryptospiridiosis, micropsridial infections, and viral infections), radiation-induced colitis, colitis in the immunocompromised host (e.g., typhlitis), precancerous conditions of the colon (e.g., dysplasia, inflammatory conditions of the bowel, and colonic polyps), proctitis, inflammation associated with hemorrhoids, proctalgia fugax, and rectal fissures; liver gallbladder and/or bilary tract conditions such as cholangitis, sclerosing cholangitis, primary bilary cirrhosis, and cholecystitis; and intestinal abscess.

Depending on the specific condition or disease state to be treated, subjects may be administered the L-arginine salts of the present invention at any suitable therapeutically effective and safe dosage, as may be readily determined within the skill of the art. These L-arginine salts are, most desirably, administered in dosages ranging from about 1 to about 2000 mg per day, in a single or divided doses, although variations will necessarily occur depending upon the weight and condition of the subject being treated and the particular route of administration chosen. However, a dosage level that is in the range of about 0.1 to about 100 mg/kg, preferably between about 5 and 90 mg/kg, and more preferably between about 5 and 50 mg/kg, is most desirable. Variations may nevertheless occur depending upon the weight and conditions of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such large doses are first divided into several small doses for administration throughout the day.

The L-arginine salts of the present invention can be administered in the form of any pharmaceutical formulation, the nature of which will depend upon the route of administration. These pharmaceutical compositions can be prepared by conventional methods, using compatible, pharmaceutically acceptable excipients or vehicles. Examples of such compositions include capsules, tablets, transdermal patches, lozenges, troches, sprays, syrups, powders, granulates, gels, elixirs, suppositories, and the like, for the preparation of extemporaneous solutions, injectable preparations, rectal, nasal, ocular, vaginal etc. A preferred route of administration is the oral and rectal route.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with sweetening or flavoring agents, coloring matter and, if so desired, emulsifying and/or suspending agents, together with such diluents as water, ethanol, propylene glycol, glycerin and various combinations thereof.

The dosage form can be designed for immediate release, controlled release, extended release, delayed release or targeted delayed release. The definitions of these terms are known to those skilled in the art. Furthermore, the dosage form release profile can be effected by a polymeric mixture composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

For parenteral administration, a solution of an active L-arginine salt of 4- or 5-ASA in either sesame or peanut oil or in aqueous propylene glycol can be employed. The aqueous solutions should be suitably buffered (preferably pH greater than 8), if necessary, and the liquid diluent first rendered isotonic. The aqueous solutions are suitable for intravenous injection purposes. The preparation of all these solutions under sterile conditions is readily accomplished by standard pharmaceutical techniques well known to those skilled in the art.

The following non-limitative examples further describe and enable a person ordinarily skilled in the art to make and use the invention.

EXAMPLE 1

Synthesis of L-arginine Salt of 5-ASA (Mesalamine)

A hydrochloric solution of L-arginine (1 mmol) was added to a hydrochloric solution of mesalamine (1 mmol). The solution thus obtained was evaporated, the product was dissolved in water and the resulting solution was divided in vials of 1.5 ml each and lyophilised for 14 hours. Water content (K.F.), 2%. Melting point is in the range of 75-88° C., and, more preferably, between 81-88° C.

EXAMPLE 2

Effects of L-arginine Salt of 5-ASA (Mesalamine) in TNBS-Induced Colitis in Mice A standard experimental animal model of colitis induced by intracolonic administration of 2,4,6-trinitrobenzene sulfonic acid (TNBS) to mice is used in the following example. A detailed description of this model has been published (Santucci et al. (2003) *Gastroenterology* 124:1381-94) and is incorporated herein by reference. Briefly, 6-8 week old Balb/c mice were given TNBS intracolonically at a dose of 1.5 mg in 0.1 mL of 30% ethanol. The mice were randomized to the various treatment groups (n=6 per group). Beginning one hour later and continuing every 12 h for 5 days, the mice were treated orally with vehicle (1% carboxymethylcellulose (CMC)), mesalamine (50 mg/kg) or with an equimolar dose of L-arginine salt of mesalamine.

The mice were evaluated (blindly) on the final day of the study for the presence of diarrhea and fecal occult blood, and their body weights were measured. A "disease activity score" was calculated based on these data (0 to 4 scale, as outlined in the paper cited above). The mice were then sacrificed and a sample of the colon was excised for measurement of myeloperoxidase (MPO) activity, an indicia for granulocyte infiltration.

Figure 2:
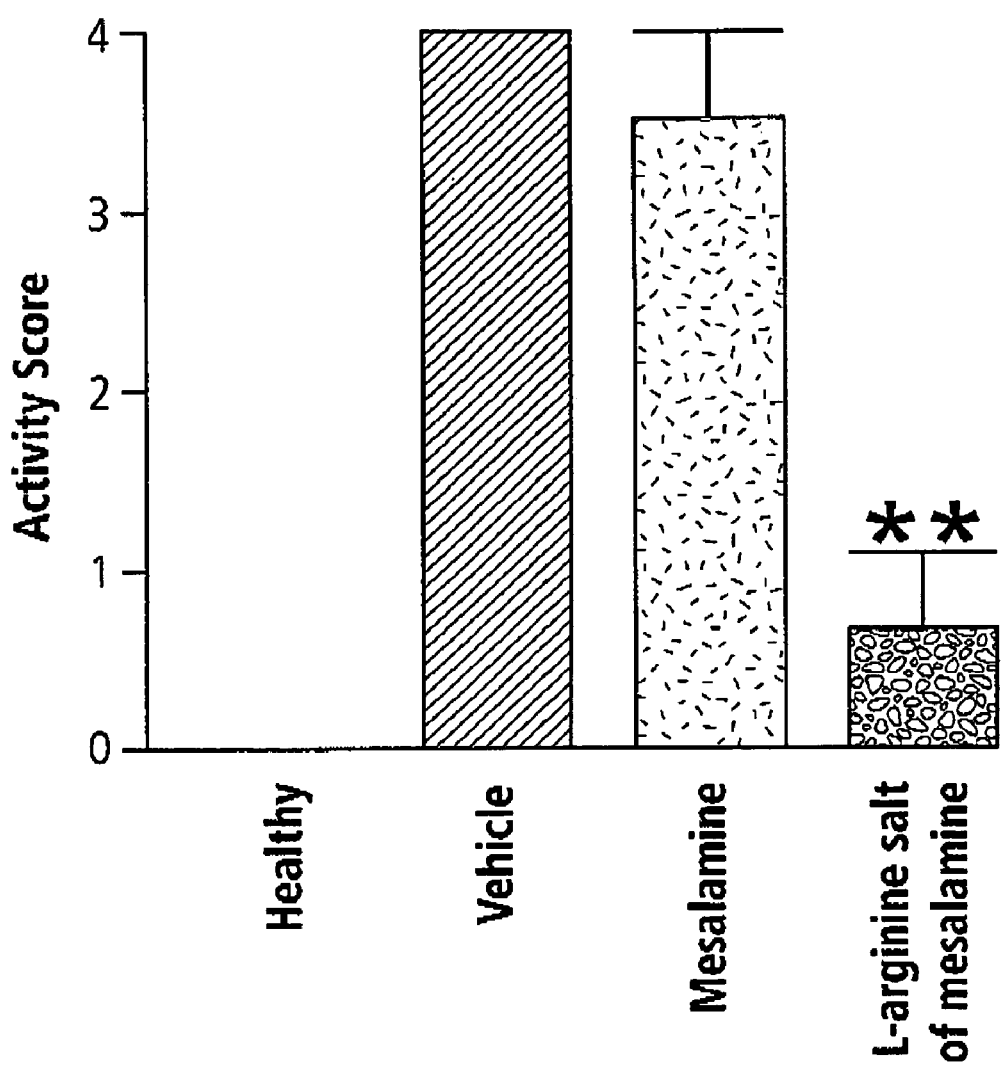
FIG. 2 shows the Disease Activity Score of mice having TNBS-induced colitis after treatment with vehicle (1% CMC), 50 mg/kg mesalamine and equimolar dose of L-arginine salt of mesalamine of the present invention.
Figure 3:
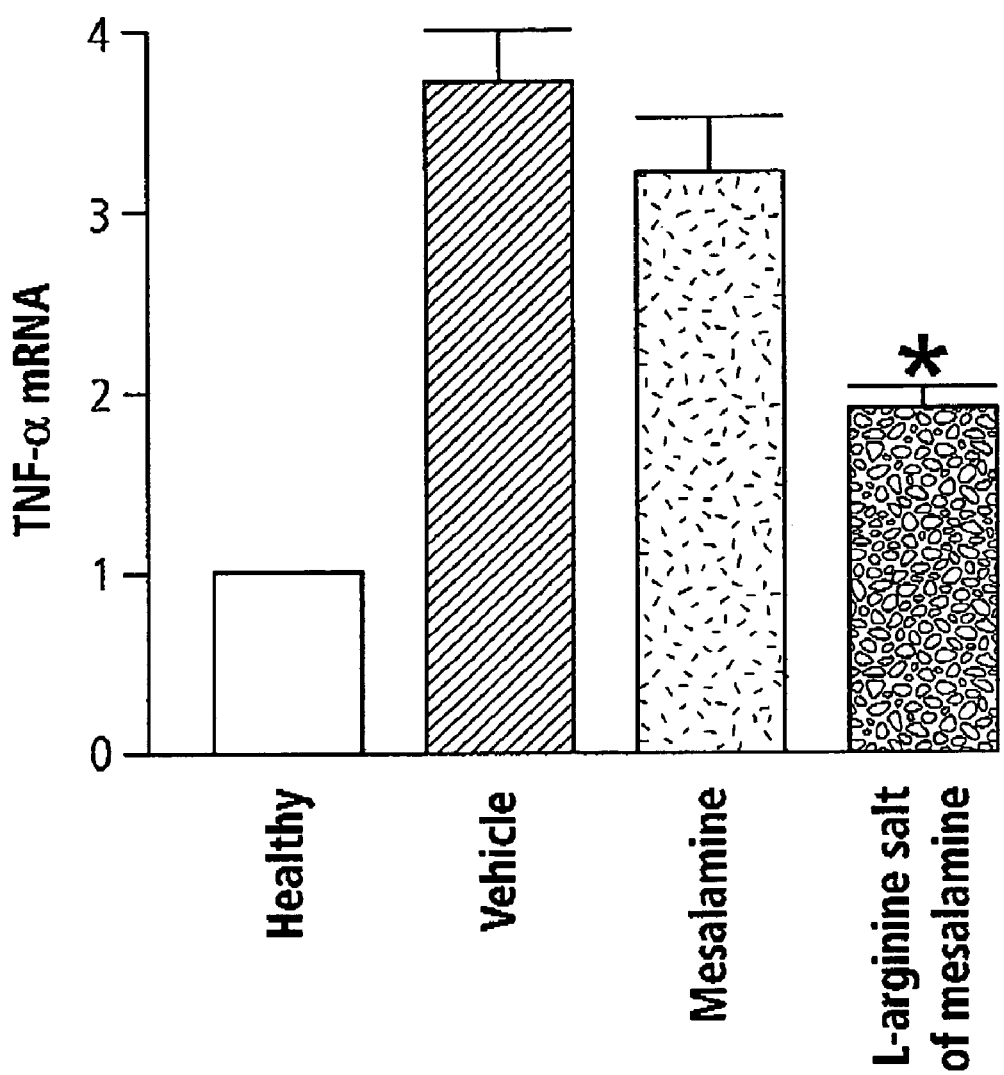
FIG. 3 shows colonic tumour necrosis factor (TNF-α) mRNA expression in mice with TNBS-induced colitis after treatment with vehicle (1% CMC), 50 mg/kg mesalamine and equimolar dose of L-arginine salt of mesalamine of the present invention.
Figure 4:
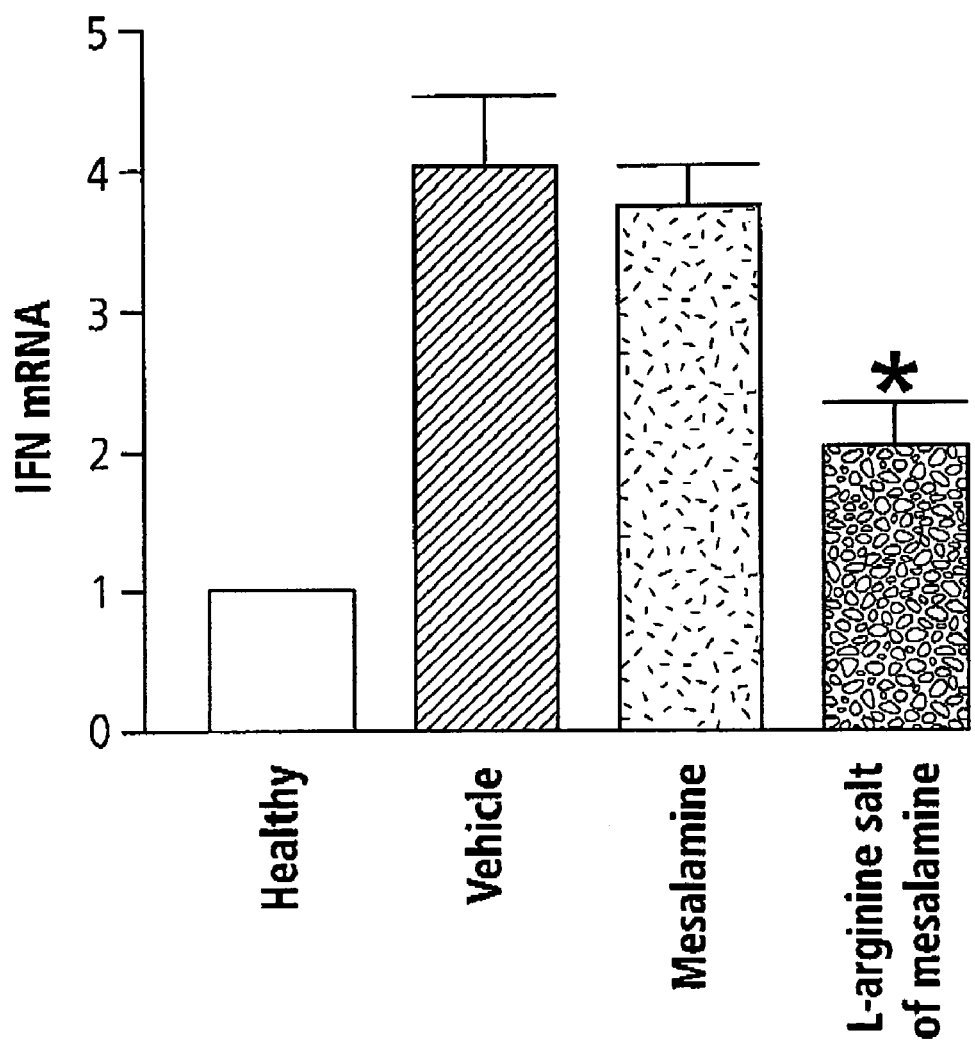
FIG. 4 shows interferon gamma (IFN-γ) mRNA expression in mice with TNBS-induced colitis after treatment with vehicle (1% CMC), 50 mg/kg mesalamine and equimolar dose of L-arginine salt of mesalamine of the present invention.
Figure 5:
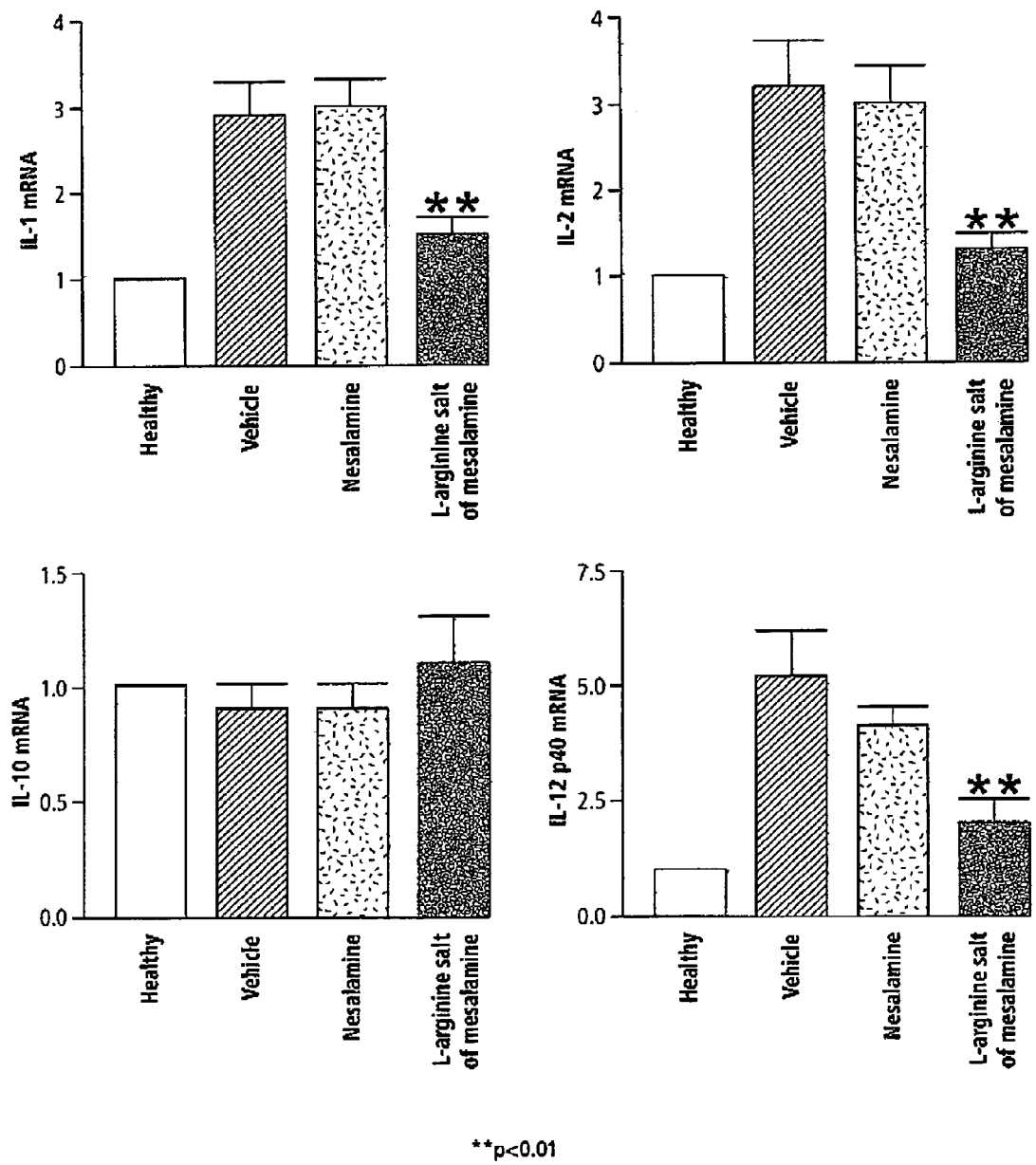
FIG. 5 shows various interleukin (IL) mRNA expression, namely, IL-1, -2, 10 and -12 mRNA, in mice with TNBS-induced colitis after treatment with vehicle (1% CMC), 50 mg/kg mesalamine and equimolar dose of L-arginine salt of mesalamine of the present invention.
Figure 6:
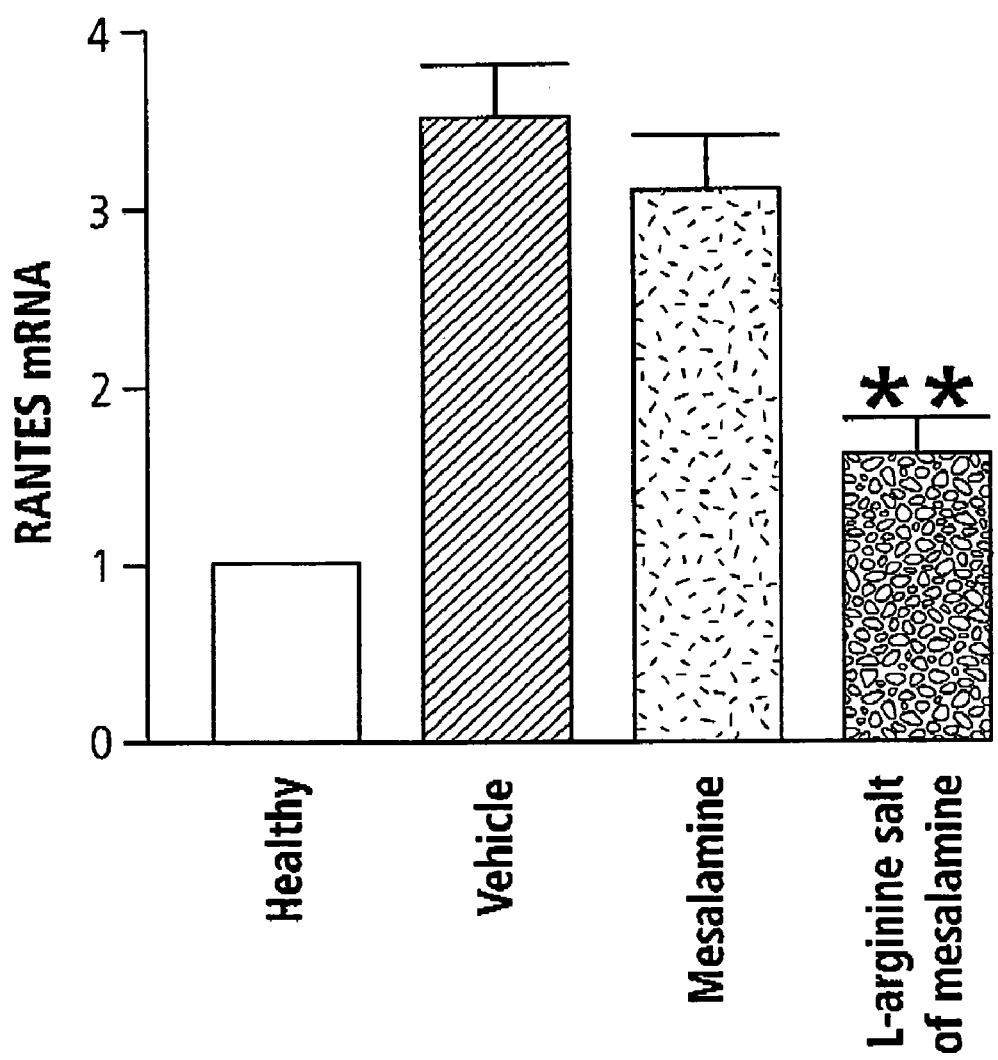
FIG. 6 shows colonic levels of RANTES mRNA in mice with TNBS-induced colitis after treatment with vehicle (1% CMC), 50 mg/kg mesalamine and equimolar dose of L-arginine salt of mesalamine of the present invention.
Figure 7:
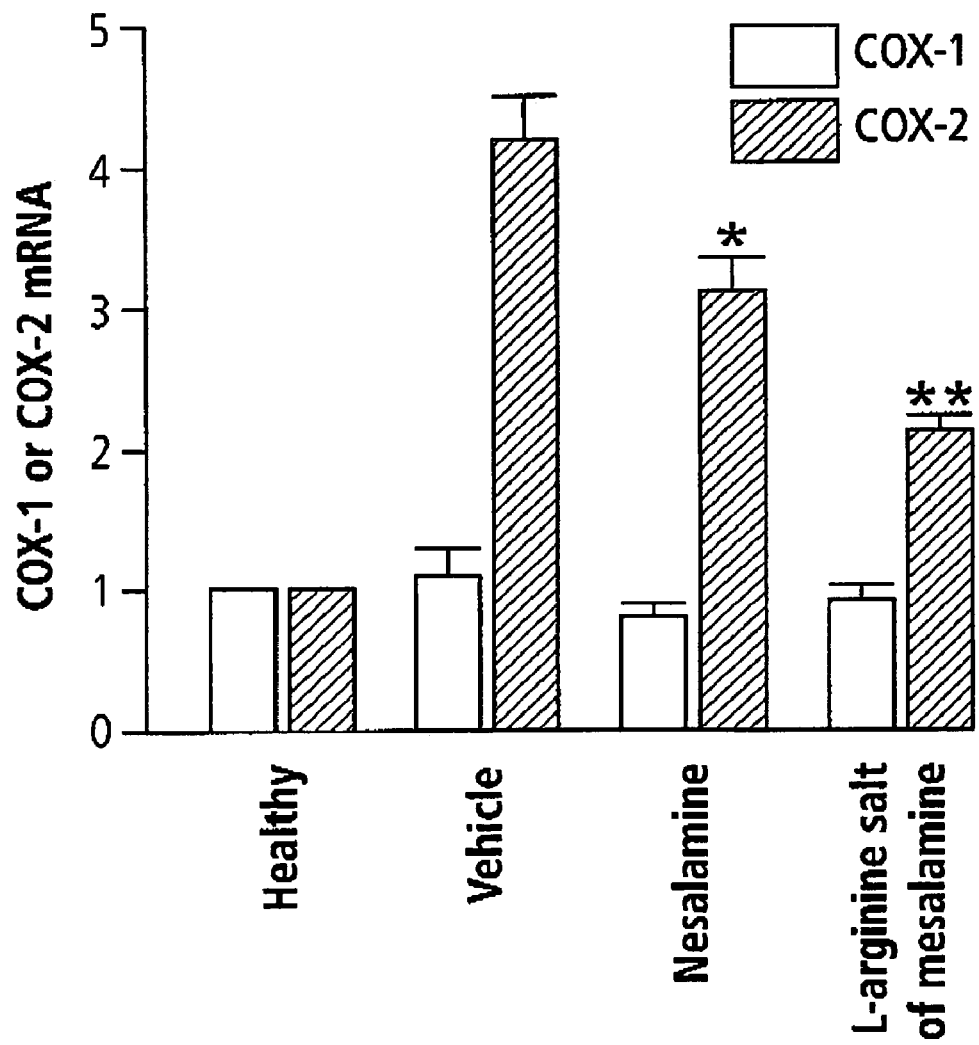
FIG. 7 shows colonic COX-1 and COX-2 mRNA expression in mice with TNBS-induced colitis after treatment with vehicle (1% CMC), 50 mg/kg mesalamine and equimolar dose of L-arginine salt of mesalamine of the present invention.
Figure 8:
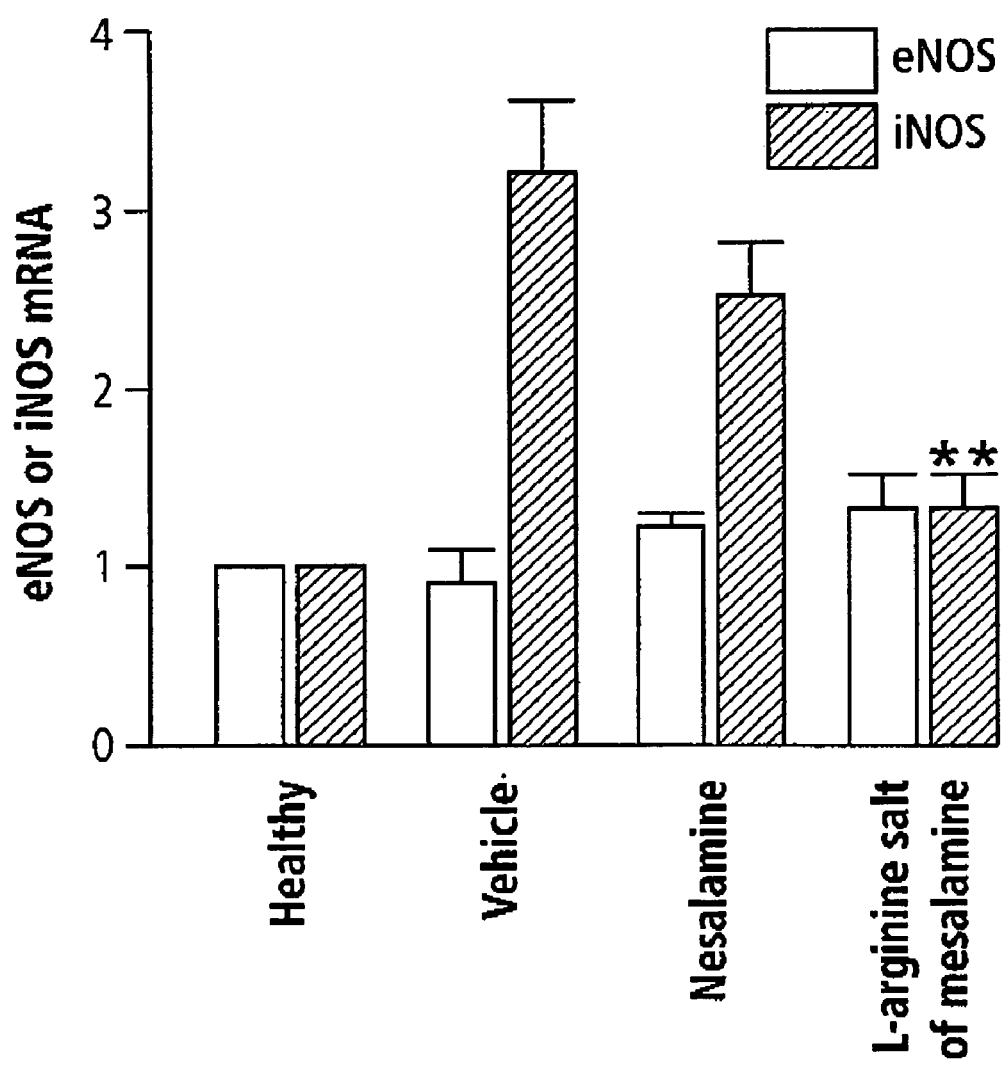
FIG. 8 shows colonic eNOS and iNOS mRNA expression in mice with TNBS-induced colitis after treatment with vehicle (1% CMC), 50 mg/kg mesalamine and equimolar dose of L-arginine salt of mesalamine of the present invention.

The disease activity scores, as shown in FIG. 1, illustrate that the L-arginine salt of mesalamine was superior to mesalamine alone in reducing the disease at an equimolar dose of 50 mg/kg. Further, the L-arginine salt of mesalamine was superior to mesalamine alone in reducing MPO activity at an equimolar dose of 50 mg/kg, as shown in FIG. 2.

EXAMPLE 3

Effects of Mesalamine and L-Arginine Salt of Mesalamine on Inflammation in TNBS-Induced Colitis in Mice The same model was used as described above. In this example, the effects of mesalamine (50 mg/kg) were compared to those of equimolar doses of L-arginine salt of mesalamine. Tissues were processed for measurement of a number of genes for inflammatory cytokines and other mediators.

In particular, mRNA expression in mice of tumour necrosis factor-alpha (TNF-α), interferon gamma (IFN-γ), colonic interleukin (IL)-1, IL-2, IL-10, IL-12 p40, RANTES, cyclooxygenase (COX)-1, COX-2, constitutive endothelial nitric oxide synthase (eNOS), and inducible NOS (iNOS) was measured as described in Wallace et al. (1999) *Gastroenterology* 117: 557-566, incorporated herein by reference.

Briefly, reverse transcription-polymerase chain reaction (RT-PCR) was used to detect and quantify mRNA of the particular cytokine/chemokine/enzyme. Glyceraldehyde-3-phosphate dehydrogenase (GAPDH) was used as the "housekeeping gene" for mRNA expression (i.e., as an internal control). For each sample, the ratio of the amplification of the target gene to the amplification of GAPDH (expression of each is measured by performing densitometry on gels) was obtained. Comparisons were then made between the relative amplification (expression) of the target gene in tissues for the treatment groups in comparison to the expression in tissues from healthy controls. Thus, the data shown in the following FIGS. represent the relative expression of the target gene (normalized to GAPDH expression) as a ratio to the expression in healthy controls.

The results are shown in FIGS. 3 to 8. It is noteworthy that the L-arginine salt of mesalamine was superior to mesalamine in every endpoint. It is particularly interesting that L-arginine salt of mesalamine suppressed expression of mRNA for several pro-inflammatory cytokines and chemokines that have been implicated in the pathogenesis of inflammatory bowel disease. However, L-arginine salt of mesalamine did not suppress expression of IL-10 mRNA, which is an anti-inflammatory cytokine.

In addition, L-arginine salt of mesalamine suppressed both COX-1 and COX-2 mRNA. COX-1 and COX-2 are involved in the synthesis of prostaglandins, which are important in inflammation. Further, L-arginine salt of mesalamine also suppressed eNOS and iNOS mRNA. Both eNOS and iNOS have been implicated in diseases of the GI tract.

EXAMPLE 4

Figure 9:
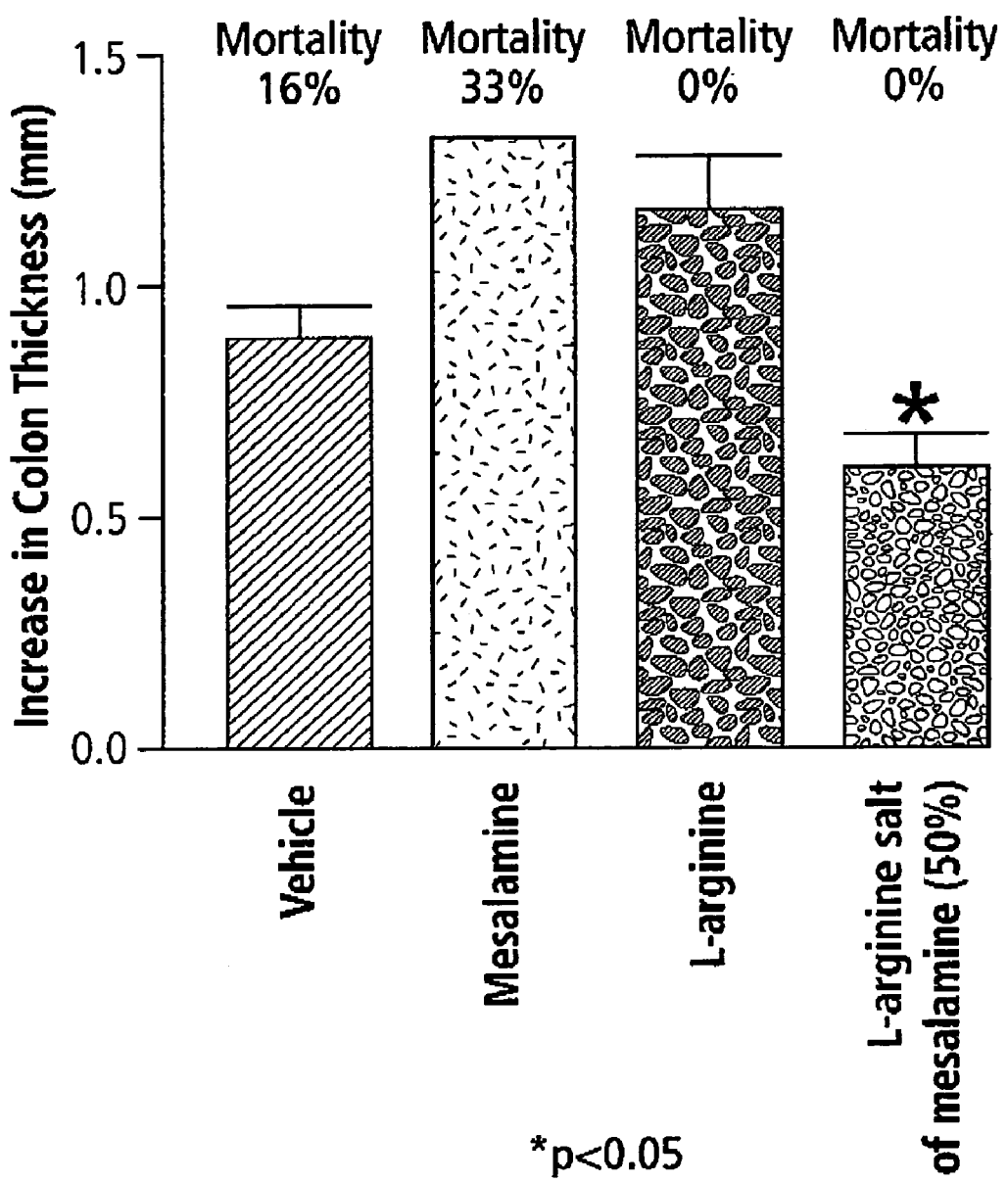
FIG. 9 shows colitis-associated edema in mice with TNBS-induced colitis after treatment with vehicle (1% CMC), 50 mg/kg mesalamine, equimolar L-arginine and 50% of the equimolar dose of L-arginine salt of mesalamine of the present invention.
Figure 10:
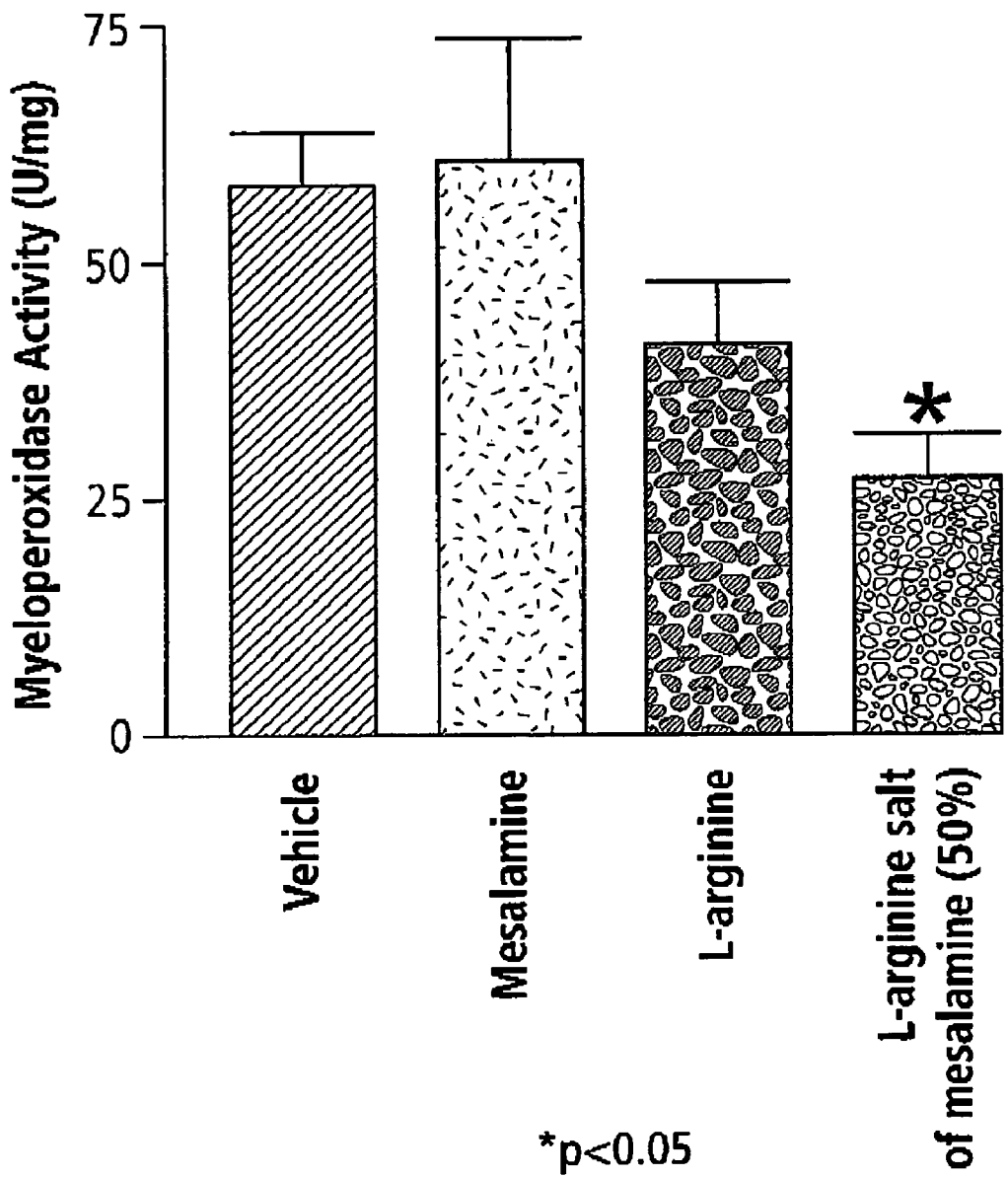
FIG. 10 shows colitis-associated granulocyte infiltration (MPO activity) in mice with TNBS-induced colitis after treatment with vehicle (1% CMC), 50 mg/kg mesalamine, equimolar L-arginine and 50% of the equimolar dose of L-arginine salt of mesalamine of the present invention.
Figure 11:
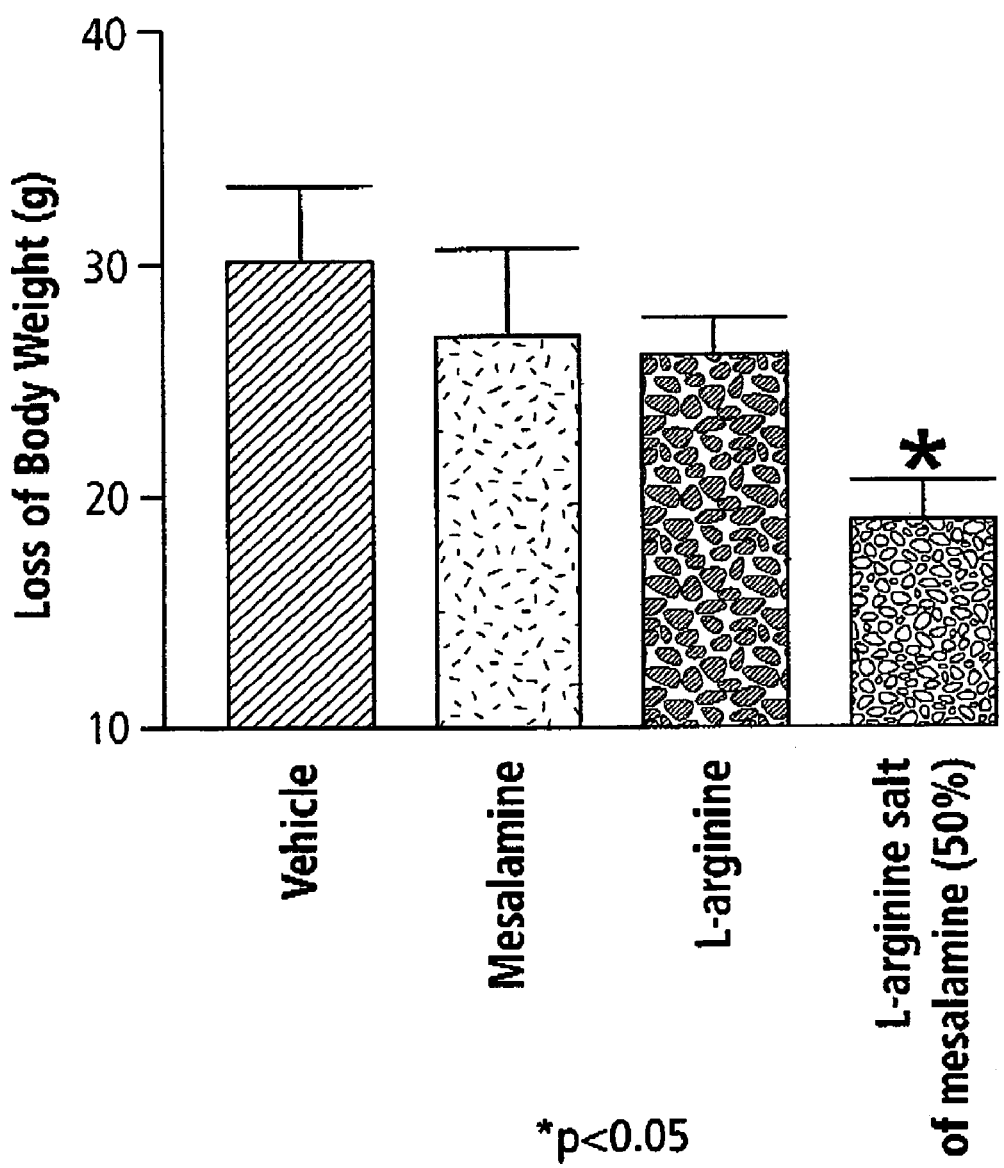
FIG. 11 shows body weight loss in mice with TNBS-induced colitis after treatment with vehicle (1% CMC), 50 mg/kg mesalamine equimolar L-arginine and 50% of the equimolar dose of L-arginine salt of mesalamine of the present invention.

Comparison of the Effects of L-Arginine Salt of Mesalamine Versus Mesalamine alone and L-Arginine Alone in TNBS-Induced Colitis in Rats Colitis was induced in male, Wistar rats by intracolonic administration of TNBS, as outlined in Wallace et al. (1990), *Am J Physiol.* 258: G527-G534, incorporated herein by reference. Briefly, beginning 1 h later and continuing at 12 h intervals for 4 days, the rats were treated with vehicle (1% CMC), mesalamine (50 mg/kg), L-arginine (equimolar) or L-arginine salt of mesalamine (50% of the equimolar dose). Changes in body weight were recorded, as were incidences of mortality. At the end of the study, the colon was excised and the thickness of the bowel wall was measured with digital callipers, as an index of edema. Also, a sample of tissue was processed for measurement of myeloperoxidase (MPO) activity, as an index of granulocyte infiltration. The results are summarized in FIGS. 9, 10 and 11.

In each case, L-arginine salt of mesalamine was found to be superior to both mesalamine and L-arginine. Note that the dose of L-arginine salt of mesalamine used contained only half the amount of mesalamine and L-arginine as the comparator groups. Furthermore, the data show that the effectiveness of L-arginine salt of mesalamine is not merely the additive effect of mesalamine alone and L-arginine alone. It is clear that the L-arginine plus mesalamine in a salt form provides a synergistic reduction of the above indicia of inflammation.

EXAMPLE 5

Anti-Oxidant Properties of L-Arginine Salt of Mesalamine, Mesalamine and L-Arginine One of the mechanisms through which mesalamine is thought to provide benefit in the treatment of inflammatory bowel disease is through scavenging of free radicals. Therefore, the anti-oxidant activity of mesalamine was compared to that of L-arginine salt of mesalamine and L-arginine. Anti-oxidant activity of the test drugs was measured in an in vitro assay that employs a coloured, stable free radical as outlined in Vaananen, P. M. et al. (1992) *Inflammation* 16: 227-240 and Smith, R. C. et al. (1987) *Free Rad. Biol. Med.* 3: 251-257, both incorporated herein by reference. Drugs with anti-oxidant activity reduce this reagent resulting in a change in colour, which can be detected spectrophotometrically. A range of concentrations of L-arginine salt of mesalamine, mesalamine and L-arginine, all prepared in ethanol, were tested and the concentration that reduced the levels of the free radical by 50% were calculated. Results are shown in Tables 1 and 2 below.

TABLE 1

| | % Free Radical Scavenging | | | | | |
|---|---|---|---|---|---|---|
| Sample | 10 mM | 3 mM | 1 mM | 0.3 mM | 0.1 mM | 0.03 mM |
| Mesalamine | 100 | 96.1 | 50.3 | 23.6 | X | 2.2 |
| L-arginine | 0 | 0 | 0 | 0 | 0 | 0 |
| ATB-428 | 100 | 100 | 96.3 | 57.7 | 23.9 | 5.2 |

Results are means of quadruplicate experiments. Missing data (X) represent cases where there was a large variance among replicates.

TABLE 2

| 50% Inhibitory Concentrations | |
|---|---|
| Sample | IC50 (mM) |
| Mesalamine | 1.254 |
| L-arginine | >10 |
| ATB-428 | 0.407 |

These results suggest that L-arginine salt of mesalamine is about three-times more potent as an anti-oxidant as is mesalamine itself. L-arginine did not exhibit any anti-oxidant activity in this assay at concentrations of up to 10 mM. To put the antioxidant concentrations into clinical perspective, luminal concentrations of mesalamine in the colon following oral ingestion of 500 mg of this drug will reach 1 mM (Goebell, H. et al. (1993) Gut 34: 669-675). The usual dose of mesalamine is 2-4 g/day, divided into ~3 doses over the course of a day.

What is claimed is:

1. The L-arginine salt of 4-aminosalicylic acid.
2. The L-arginine salt of 5-aminosalicylic acid.
3. A pharmaceutical composition comprising a compound according to claim 1 or claim 2 and a pharmaceutically acceptable excipient or carrier.
4. A method of treating an inflammatory condition of the gastrointestinal tract in a subject in need of such treatment, said method comprising administering to the subject an amount effective to treat the inflammatory condition of the gastrointestinal tract of a compound according to claim 1 or claim 2.
5. The method according to claim 4, wherein the inflammatory condition of the gastrointestinal tract is Crohn's disease.
6. The method according to claim 4, wherein the inflammatory condition of the gastrointestinal tract is ulcerative colitis.
7. The method according to claim 4, wherein the inflammatory condition of the gastrointestinal tract is irritable bowel syndrome.

* * * * *